(12) United States Patent  
Schindler

(10) Patent No.: US 7,152,606 B1  
(45) Date of Patent: Dec. 26, 2006

(54) PROSTHETIC DEVICE

(76) Inventor: Randi Lynn Schindler, 1970 Benecia Ave., Los Angeles, CA (US) 90025

( * ) Notice: Subject to any disclaimer, the term of this patent is extended or adjusted under 35 U.S.C. 154(b) by 0 days.

(21) Appl. No.: 09/152,992

(22) Filed: Sep. 14, 1998

(51) Int. Cl.  
*A61F 13/00* (2006.01)

(52) U.S. Cl. .......................... 128/889; 128/890; 450/81

(58) Field of Classification Search ................ 128/846, 128/889, 890; 450/36–41; 604/366, 370, 604/377, 378, 381  
See application file for complete search history.

(56) References Cited

U.S. PATENT DOCUMENTS

| | | | |
|---|---|---|---|
| 1,165,275 A * | 12/1915 | Montgomery | 128/890 |
| 2,131,457 A | 9/1938 | Tachat | |
| 2,728,079 A | 12/1955 | Williams | |
| 2,793,369 A | 5/1957 | Panighini | |
| 2,869,553 A | 1/1959 | D'Or | |
| 3,276,449 A | 10/1966 | Morgan | |
| 3,280,818 A | 10/1966 | Pankey et al. | |
| 3,749,102 A | 7/1973 | Wynants | |
| 3,825,014 A * | 7/1974 | Wroten | 128/360 |
| 4,195,639 A * | 4/1980 | Lee | 128/890 |
| 4,333,471 A * | 6/1982 | Nakai | 128/890 |
| 4,343,313 A | 8/1982 | Le Jeune | |
| 4,640,288 A * | 2/1987 | Hattori | 450/81 |
| 4,870,977 A * | 10/1989 | Imonti | 128/890 |
| 4,992,074 A | 2/1991 | Diaz | |
| 5,032,103 A * | 7/1991 | Larsson | 128/890 |
| 5,394,889 A * | 3/1995 | Morrissey et al. | 128/845 |
| 5,782,672 A | 7/1998 | Woodley | |
| 6,231,424 B1 | 5/2001 | Valentin | |
| 6,758,720 B1 | 7/2004 | Chen | |
| 6,814,648 B1 | 11/2004 | Chong | |

OTHER PUBLICATIONS

"Breast Petals" product literature, Fashion Forms, Ventura, California (1998).  
Fashion Forms, Silicone Enhancers, (1997), 11 pages, Ventura, California.

* cited by examiner

*Primary Examiner*—Michael A. Brown  
(74) *Attorney, Agent, or Firm*—Law Offices of David L. Hoffman

(57) ABSTRACT

A method of covering a nipple on a human breast, the nipple cover having a center and including a flexible material for conforming to a human breast, the method including the method steps of placing the nipple cover directly on a human breast so as to cover at least about one half and less then all of the breast, with the center of the cover proximate the nipple; the nipple cover having a first thickness proximate the center and a second thickness proximate a periphery thereof, the thickness of the nipple cover gradually tapering from the first thickness to the second thickness, wherein the method further includes the step of being the nipple cover on the breast such that the periphery of the cover blends smoothly with a curved portion of the breast while concealing a nipple shape.

5 Claims, 2 Drawing Sheets

PROSTHETIC DEVICE

BACKGROUND OF THE INVENTION

1. Field of the Invention

The present invention relates to the field of prosthetic devices, and more particularly to a new, unique and attractive device which is especially adapted to conceal women's nipples and which is simple in construction and consequently economical to manufacture.

2. Prior Art

Women may often choose to wear a brassiere or the like on their breasts in order to provide a pleasing contour to their figure by the effect of moderate pressure provided by the brassiere. There are times, however, when the use of a brassiere is undesirable. In the summertime, for example thin garments ore often worn, and the brassiere is visible through clothing, and this can present an unsightly appearance. The only viable alternative to this is for a woman to forego wearing a brassiere entirely. At the same time, many women do not want to dispense with the brassiere. This is because the brassiere provides a certain level of modesty and privacy when it is worn. This privacy is lost without the use of the brassiere. In particular, the brassiere will cover the nipple and areola of a woman. Without the brassiere, the woman's nipple is likely to be visible through the woman's clothing. For many women, this is simply not an acceptable alternative.

The brassiere also presses upon the breasts and body of the user by its belts and straps with a resultant inherent discomfort and inconvenience. Moreover, the use of a brassiere can be very uncomfortable in hot weather and can cause excessive perspiration.

SUMMARY OF THE PRESENT INVENTION

The present invention provides a prosthetic device which is intended to overcome the limitations of the prior art. In particular, the present invention provides a nipple cover which is easy to manufacture and use. The nipple cover provides an effective means of covering a woman's breast so that the nipple is not exposed or visible through thin or sheer clothing. The present invention can therefore be used in instances where the use of a brassiere is not practical. The nipple cover is also an improvement over the use of a brassiere because it is smaller in size and bulk. it also lacks the use of straps and belts which can cause discomfort. The present invention is therefore more comfortable and easier to wear.

DETAILED DESCRIPTION OF THE PREFERRED EMBODIMENT

A prosthetic device which functions as a nipple cover will be described. In the following description, for the purposes of explanation, specific construction details, arrangements, and materials are set forth in order to provide a more thorough understanding of the present invention. It will be apparent to those skilled in the art, however, that the present invention may be practiced without these specific details. In other instances, well known manufacturing methods and structures have not been described in detail so as not to obscure the present invention unnecessarily.

Figure 1:
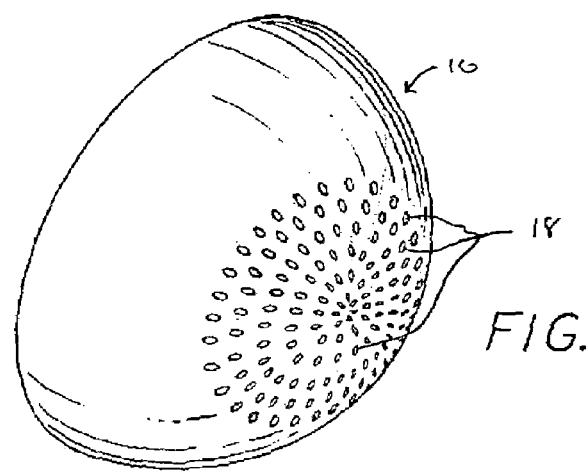
FIG. 1 is a perspective view of the preferred embodiment of the prosthetic device of the present invention.

Referring first to FIG. 1, an illustration of the nipple cover 10 of the present invention is shown. As can be seen, the nipple cover 10 has a shape that generally approximates the shape of a female human breast. The present invention consists of a flexible, reusable and flesh-colored apparatus that covers the nipple so that a woman can go braless or wear a thin bra or lingerie. The device will be soft enough to conform to the woman's figure, yet hard enough so that it will not be affected by the shape of the woman's own nipples.

Referring again to FIG. 1, the nipple cover 10 of the present invention has a generally hemispherical shape. It is not solid, but rather is hollow on the inside. The present invention is not intended to replace or enhance a woman's breast. Its' intended purpose is to provide a cover for the nipple. The present invention is also not intended to provide support to the breast, as with a traditional brassiere. Therefore, the nipple cover can be manufactured from a relatively thin material.

Figure 2:
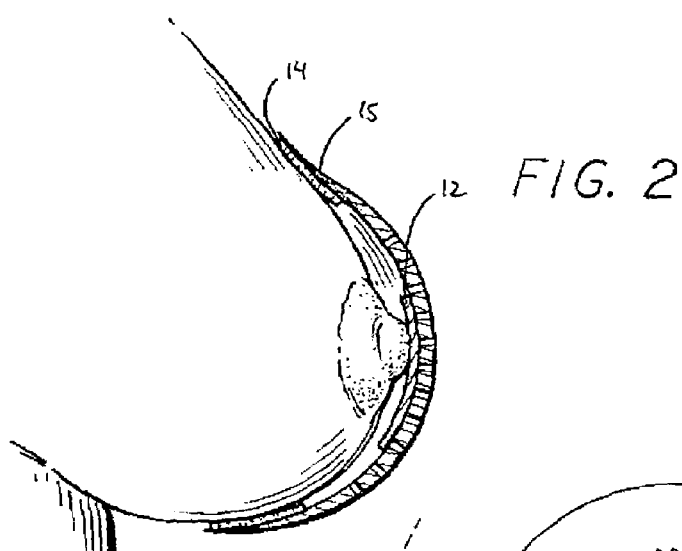
FIG. 2 is a cross-sectional view of the prosthetic device.

Referring next to FIG. 2, a cross sectional view of the nipple cover is shown. The nipple cover, as noted above is hollow inside. The thickness of the nipple cover is not uniform. The edges 15 of the device will gradually taper to be thinner near the edges 15. This will allow the nipple cover to blend with the breast surface (as shown in FIG. 2) for a continuous smoothness.

Figure 3:
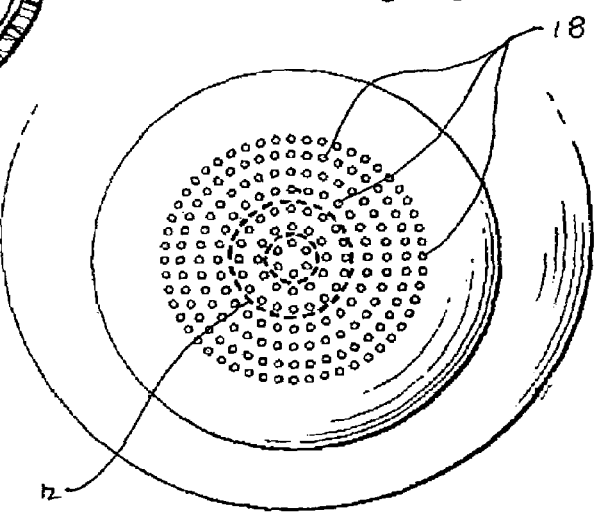
FIG. 3 is a front elevation view of the prosthetic device of the present invention showing how it attaches to the human breast.
Figure 4:
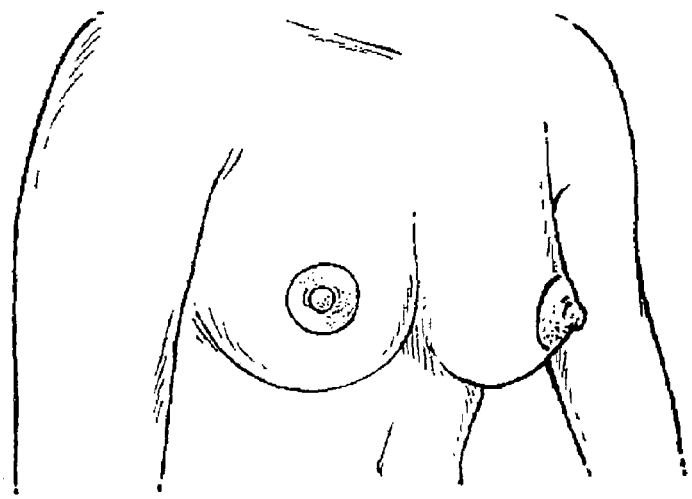
FIG. 4 is an illustration of a human torso without the present invention attached.
Figure 5:
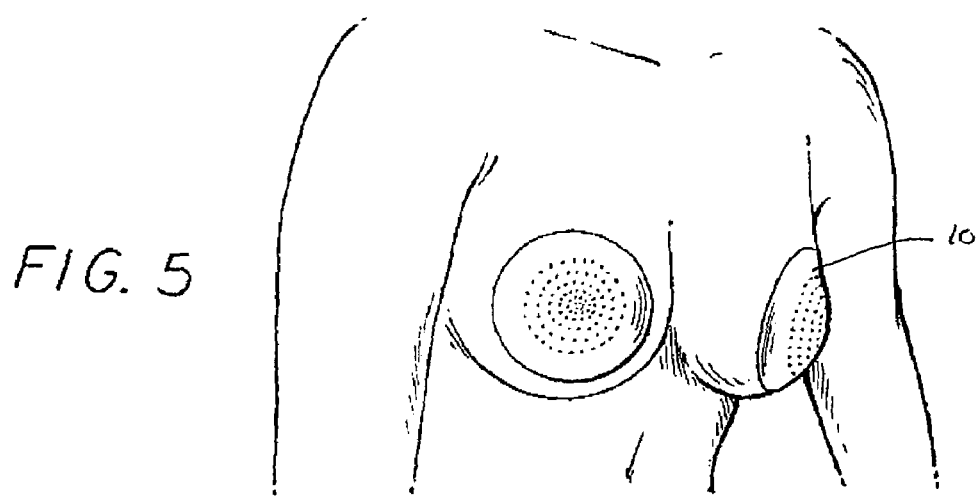
FIG. 5 is an illustration of a human torso having the present invention attached.

An absorbent pad 12 is located on the inner portion of the nipple cover, near the center of the device. The absorbent pad 12 is manufactured from a thin, cell-like, material. The purpose of the pad is to absorb perspiration and moisture from the user's skin. The device will also include a number of tiny holes 18. The holes are best shown in FIGS. 1 and 3. The holes further allow perspiration to be released, thereby increasing the comfort of the user. The holes are concentrated near the center of the nipple cover.

The nipple cover is of sufficient size such that it can cover a user's entire nipple and areola. The cover will also extend a short distance beyond this area to ensure complete coverage. In the preferred embodiment, the nipple cover will extend approximately one-eighth to one-fourth of an inch beyond the areola. The exact size of the nipple cover, however will vary, as will be apparent to those skilled in the art.

The human breast takes on a wide variety of shapes and sizes, and it therefore anticipated that the nipple cover will be constructed in range of different sizes and styles. The illustration of FIG. 1 is therefore intended to be for illustrative purposes only, and is not intended to provide a specific limitation on the size and style of the present invention. It is anticipated that that nipple cover will also be manufactured in a range of different colors, from dark to light. This will enable the nipple cover to match the skin color of the person wearing it.

The preferred embodiment of the nipple cover includes an adhesive material 14 which will permit it to more easily attached to the breast. The adhesive material may be tape, glue or other suitable material. In the preferred embodiment, the adhesive will be non-toxic and hypo-allergenic. Referring again to FIG. 2, the adhesive 14 does not completely cover the inside surface of the nipple cover. The adhesive is located only along the outer edges of the cover 10. The adhesive forms an annular ring around the inner edges of the device. In an alternative embodiment, the adhesive may be omitted.

The present invention may be manufactured for a single use, or it may be reusable. If the device is manufactured for a single use, then it will have the adhesive permanently attached to the inner surface of the nipple cover. If the device is reusable, then the adhesive can be removed after each use. A new layer of adhesive can then be applied on the surface after cleaning.

The present invention will be manufactured from a soft "skin-like" rubbery and flexible material. The material will be flexible so that the device can conform to the shape of the user's breast. The material must be soft in feel and look. At the same time it must be solid enough not to crinkle or change it's smoothness if the user's nipple hardens underneath. The preferred embodiment of the present invention utilizes plastic urethane. It will be apparent to those skilled in the art that other, equivalent materials may also be used with equal effectiveness. The specific material chosen may vary from the preferred embodiment.

Figure 6:
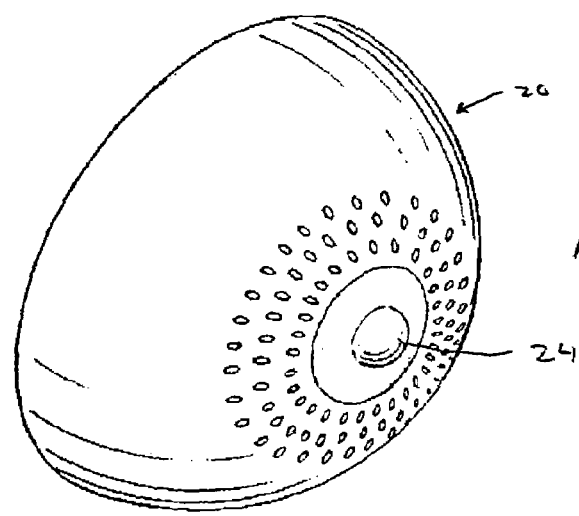
FIG. 6 is a perspective view of an alternative embodiment of the present invention.

An alternative embodiment of the invention is illustrated in FIG. 6. In the alternative embodiment, the prosthetic device 20 also covers the breast, and it hides the woman's own nipples. The outer surface of the nipple cover, however, includes a simulated, or synthetic nipple 24. This alternative embodiment can be used when the woman desires to have the appearance of an erect nipple visible through her clothing. The synthetic nipple is manufactured by including a protrusion on the nipple cover in the approximate location where the woman's own nipple would naturally be located. The size and look of the synthetic nipple can be varied as a matter of design choice. For example, the size of the nipple may be exaggerated in some instances.

The description of the present invention has been made with respect to specific arrangements and constructions of a nipple cover. It will be apparent to those skilled in the art that the foregoing description is for illustrative purposes only, and that various changes and modifications can be made to the present invention without departing from the overall spirit and scope of the present invention. The full extent of the present invention is defined and limited only by the following claims.

What is claimed is:

1. A method of covering a nipple on a human breast, the nipple cover having a center and comprising a flexible material for conforming to a human breast, the method comprising the steps of:

placing the nipple cover directly on a human breast so as to cover at least about one half and less than all of the breast, with the center of the cover proximate the nipple;

the nipple cover having a first thickness proximate the center and a second thickness proximate a periphery thereof, and the thickness of the nipple cover gradually tapering from the first thickness to the second thickness, wherein the method further includes the step of bending the nipple cover on the breast such that the periphery of the cover blends smoothly with a curved portion of the breast while concealing a nipple shape.

2. The method of claim 1, further comprising a step of selecting a nipple cover from a plurality of colors of nipple covers and from a plurality of shapes and sizes for covering at least about one half of the breast and less than all of the breast.

3. The method of claim 2, further comprising a step of wearing clothing in contact with an outer surface of the nipple cover without a brassiere.

4. The method of claim 1, wherein in the step of placing, the cover is affixed to the human breast by adhesive.

5. The method of claim 1 further comprising a step of selecting the nipple cover with a color matching a skin color of the breast upon which the cover is placed.

* * * * *